United States Patent
Lee et al.

(10) Patent No.: US 9,877,659 B2
(45) Date of Patent: *Jan. 30, 2018

(54) SENSING SYSTEM AND METHOD FOR PHYSIOLOGY MEASUREMENTS

(71) Applicant: INDUSTRIAL TECHNOLOGY RESEARCH INSTITUTE, Hsinchu (TW)

(72) Inventors: Yen-Hsien Lee, Zhongli (TW); Hong-Dun Lin, Pingzhen (TW); Wen-Jen Tseng, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 741 days.

This patent is subject to a terminal disclaimer.

(21) Appl. No.: 14/335,216

(22) Filed: Jul. 18, 2014

(65) Prior Publication Data

US 2014/0343393 A1 Nov. 20, 2014

Related U.S. Application Data

(63) Continuation-in-part of application No. 13/743,319, filed on Jan. 16, 2013, now Pat. No. 9,134,404, and a
(Continued)

(30) Foreign Application Priority Data

Nov. 30, 2012 (TW) .............................. 101145184 A

(51) Int. Cl.
*A61B 5/021* (2006.01)
*A61B 5/00* (2006.01)
(Continued)

(52) U.S. Cl.
CPC ........ *A61B 5/02125* (2013.01); *A61B 5/0004* (2013.01); *A61B 5/0082* (2013.01);
(Continued)

(58) Field of Classification Search
None
See application file for complete search history.

(56) References Cited

U.S. PATENT DOCUMENTS 4,617,567 A 10/1986 Chan
4,846,189 A 7/1989 Sun
(Continued)

FOREIGN PATENT DOCUMENTS

CN 101578067 A 11/2009
CN 103027670 A 4/2013
(Continued)

OTHER PUBLICATIONS

European Patent Office, Written Opinion accompanying Search Report, Patent Application Serial No. EP14178472, dated Mar. 10, 2015, Europe.
(Continued)

*Primary Examiner* — Jacqueline Cheng
*Assistant Examiner* — Jairo Portillo
(74) *Attorney, Agent, or Firm* — Rabin & Berdo, P.C.

(57) ABSTRACT

A sensing system for physiology measurements comprises a transmission end including a measuring signal generating module having at least one overshoot and undershoot wave generating circuits and a transmitting antenna module having at least one transmitting antenna; a receiving end having a plurality of receiving antennae with each receiving antenna receiving a reflected signal reflected by a target object; and a plurality of signal analyzing modules to generate a plurality of object active state signals by analyzing the reflected signal from each receiving antenna and transmit the plurality
(Continued)

of object active state signals to a digital signal processor. Wherein each overshoot and undershoot wave generating circuit generates a measuring signal with overshoot and undershoot waves according to an inputted Pulse Width Modulation signal, and each transmitting antenna emits the measuring signal to the target object.

20 Claims, 16 Drawing Sheets

Related U.S. Application Data continuation-in-part of application No. 13/713,768, filed on Dec. 13, 2012.

(60) Provisional application No. 61/892,174, filed on Oct. 17, 2013.

(51) Int. Cl.
| | | |
|---|---|---|
| A61B 5/03 | (2006.01) | |
| G01S 13/10 | (2006.01) | |
| G01S 13/58 | (2006.01) | |
| G01S 7/03 | (2006.01) | |
| G01S 13/88 | (2006.01) | |
| H01Q 1/36 | (2006.01) | |
| H01Q 21/28 | (2006.01) | |

(52) U.S. Cl.
CPC ............. *A61B 5/031* (2013.01); *A61B 5/725* (2013.01); *A61B 5/7278* (2013.01); *G01S 7/03* (2013.01); *G01S 13/106* (2013.01); *G01S 13/58* (2013.01); *G01S 13/88* (2013.01); *H01Q 1/36* (2013.01); *H01Q 21/28* (2013.01)

(56) References Cited

U.S. PATENT DOCUMENTS

| | | | |
|---|---|---|---|
| 5,309,916 | A | 5/1994 | Hatschek |
| 5,361,070 | A | 11/1994 | McEwan |
| 5,766,208 | A | 6/1998 | McEwan |
| 5,790,015 | A | 8/1998 | Iitsuka |
| 5,825,323 | A | 10/1998 | Heide |
| 6,215,438 | B1 | 4/2001 | Oswald et al. |
| 6,426,716 | B1 | 7/2002 | McEwan |
| 6,492,933 | B1 | 12/2002 | McEwan |
| 6,753,780 | B2 | 6/2004 | Li |
| 6,852,083 | B2 | 2/2005 | Caro et al. |
| 6,932,772 | B2 | 8/2005 | Kan |
| 6,939,299 | B1 | 9/2005 | Petersen et al. |
| 6,967,612 | B1 | 11/2005 | Gorman et al. |
| 7,427,268 | B2 | 9/2008 | Millay et al. |
| 7,504,992 | B2 | 3/2009 | Pilcher, Jr. et al. |
| 7,674,231 | B2 | 3/2010 | McCombie et al. |
| 7,725,150 | B2 | 5/2010 | Tupin, Jr. et al. |
| 7,952,515 | B2 | 5/2011 | McEwan |
| 8,444,568 | B2 | 5/2013 | Antonelli et al. |
| 2005/0068228 | A1 | 3/2005 | Burchfiel |
| 2008/0045847 | A1 | 2/2008 | Farag et al. |
| 2008/0146944 | A1 | 6/2008 | Tao et al. |
| 2009/0128247 | A1 | 5/2009 | Kobayashi et al. |
| 2009/0306525 | A1 | 12/2009 | Pinter et al. |
| 2011/0208060 | A1 | 8/2011 | Haase et al. |
| 2012/0101344 | A1 | 4/2012 | Desjardins et al. |
| 2012/0108928 | A1* | 5/2012 | Tverskoy ............. A61B 5/0059 600/324 |

FOREIGN PATENT DOCUMENTS

| | | |
|---|---|---|
| EP | 1710601 A1 | 10/2006 |
| EP | 2368492 A1 | 9/2011 |
| EP | 2517621 A1 | 10/2012 |
| JP | H11-188012 A | 7/1999 |
| JP | 2001-289940 A | 10/2001 |
| JP | 2005-102959 A | 4/2005 |
| JP | 2006-194716 A | 7/2006 |
| JP | 2007-028597 A | 2/2007 |
| JP | 2009-505710 A | 2/2009 |
| JP | 2009-216625 | 9/2009 |
| JP | 2009-236659 A | 10/2009 |
| JP | 2010-266274 A | 11/2010 |
| JP | 2011-024676 | 2/2011 |
| JP | 2011-507583 A | 3/2011 |
| JP | 2013-000177 | 1/2013 |
| JP | 2013-000177 A | 1/2013 |
| TW | 200516855 A | 5/2005 |
| TW | 200516855 A | 5/2005 |
| TW | I306023 | 2/2009 |
| TW | 201424682 A | 7/2014 |
| WO | WO-2007-023426 A2 | 3/2007 |
| WO | 2010038120 A1 | 4/2010 |

OTHER PUBLICATIONS

China Patent Office, Office Action, Patent Application Serial No. CN201410411457.1, dated Jun. 30, 2016.

Japan Patent Office, Office Action, Patent Application Serial No. JP2014-166059, dated Jul. 28, 2015, Japan.

Padilla et al., Assessment of Relationships between Blood Pressure, Pulse Wave Velocity and Digital Volume Pulse, Computers in Cardiology, 2006, p. 893-p. 896.

McCombie et al., Adaptive blood pressure estimation from wearable PPG sensors using peripheral artery pulse wave velocity measurements and multi-channel blind identification of local arterial dynamics, Proceedings of the 28th IEEE EMBS Annual International Conference, Aug. 30, 2006,p. 3521-p. 3524.

Gladdish et al., Repeatability of non-invasive measurement of intracerebral pulse wave velocity using transcranial Doppler, Clinical Science, 2005, p. 433-p. 439.

Lopez et al., Continuous blood pressure measurement in daily activities, Sensors, 2009 IEEE, ("2009 JSME-IIP/ASME-ISPS Joint Conference on Micromechatronics for Information and Precision Equipment (MIPE 20(9)", Jun. 17, 2009, pp. 2) , p. 827-p. 831.

Lin et al., Using Dual-Antenna Nanosecond Pulse Near-field Sensing Technology for Non-contact and Continuous Blood Pressure Measurement, Engineering in Medicine and Biology Society (EMBC), 2012 Annual International Conference of the IEEE, 2012, p. 219-p. 222, 34th Annual International Conference of the IEEE EMBS, San Diego, California USA, Aug. 28-Sep. 1, 2012.

Avolio et al., Arterial blood pressure measurement and pulse wave analysis—their role in enhancing cardiovascular assessment, Physiological Measurement, Nov. 26, 2009, pp. 1-48.

Woodman, et al., Interpretation of the digital volume pulse: its relationship with large and small artery compliance, Clinical Science, 2003, p. 283-p. 285.

Chen et al., Comb-Shaped Dipole Antenna on Transparent Substrat, IEEE Antennas and Propagation Society International Symposium 3A, Jul. 3-8, 2005, pp. 610-612.

Deng et al., "Comb-shaped antenna on magneto-dielectric substrate for DVB-H reception," International Conference on Microwave and Millimeter Wave Technology, Apr. 18-21, 2007, pp. 1-3.

Wu et al., "Using the Phase Change of a Reflected Microwave to Detect a Human Subject Behind a Barrier," IEEE Transactions on Biomedical Engineering 55 (1), Jan. 2008, pp. 267-272.

Lai et al., "Wireless Sensing of Human Respiratory Parameters by Low-Power Ultrawideband Impulse Radio Radar," IEEE Transactions on Instrumentation and Measurement 60 (3), Mar. 2011, pp. 928-938.

Zito et al., "SoC CMOS UWB Pulse Radar Sensor for Contactless Respiratory Rate Monitoring," IEEE Transactions on Biomedical Circuits and Systems 5 (6), Dec. 2011, pp. 503-610.

Jung et al., "Broadband flexible comb-shaped monopole antenna," IET Microwaves, Antennas & Propagation 3 (2), Mar. 2009, pp. 325-332.

(56) References Cited

OTHER PUBLICATIONS

Chinese Office Action dated Aug. 24, 2017.

* cited by examiner

SENSING SYSTEM AND METHOD FOR PHYSIOLOGY MEASUREMENTS

CROSS-REFERENCE TO RELATED APPLICATION

This is a continuation-in-part (CIP) application of U.S. application Ser. No. 13/743,319 filed on Jan. 16, 2013, the US application claims the benefit of Taiwan application Serial No. 101145184, filed on Nov. 30, 2012, the disclosure of the CIP application is incorporated by reference herein in its entirety. This is also a CIP application of U.S. application Ser. No. 13/713,768 filed on Dec. 13, 2012. The CIP application is also based on, and claims priority from, U.S. Provisional Application No. 61/892,174 filed on Oct. 17, 2013, the disclosure of which is hereby incorporated by reference herein in its entirety.

TECHNICAL FIELD

The technical field generally relates to a sensing system and a sensing method for physiology measurements.

BACKGROUND

In current blood pressure measuring devices, auscultation and electron resonance, with a cuff, are widely applied to measure the systolic and diastolic blood pressures of an artery. Therefore, the cuff needs to be inflated and deflated for indirectly measuring non-continuous blood pressure. However, when measuring the continuous blood pressure, the cuff needs to be setup correctly and be inflated and deflated repetitively, which would cause a great inconvenience to the users, and as such, the feasibility and practicality would be significantly less effective.

Sensor systems may be designed for physiology measurement or monitoring or sensing activities of a target such as wrist artery, chest artery, lung activity, and so on.

SUMMARY

The exemplary embodiments of the disclosure may provide a sensing system for physiology measurements and a sensing method thereof.

One exemplary embodiment relates to a sensing system for physiology measurements. The sensing system for physiology measurements may comprise a transmission end including a measuring signal generating module having one or more overshoot and undershoot wave generating circuits with each overshoot and undershoot wave generating circuit generating a measuring signal according to a Pulse Width Modulation (PWM) signal, and a transmitting antenna module having at least one transmitting antenna with each transmitting antenna emitting the measuring signal to a target object, wherein the measuring signal has a characteristics of a pulse wave, and overshoot and undershoot waves are also on the pulse wave; a receiving end having a plurality of receiving antennae with each receiving antenna receiving a reflected signal reflected by the target object; and a plurality of signal analyzing modules included in a plurality of sensors to generate a plurality of object active state signals by analyzing the reflected signal from the each receiving antenna, and transmit the plurality of object active state signals simultaneously or non-simultaneously to a digital signal processing (DSP) device.

Another exemplary embodiment relates to a sensing method for physiology measurements. The sensing method for physiology measurements may comprise: at a transmission end, generating, with each of a plurality of overshoot and undershoot wave generating circuits, a measuring signal according to a Pulse Width Modulation (PWM) signal, and emitting, with each of at least one transmitting antenna, the measuring signal to a target object, wherein the measuring signal has a characteristics of a pulse wave, and overshoot and undershoot waves are also on the pulse wave; at a receiving end, receiving, with each of a plurality of receiving antennae, a reflected signal reflected by the target object; and generating, by a plurality of signal analyzing modules respectively included in a plurality of sensors, a plurality of object active state signals by analyzing the reflected signal from the each receiving antenna, and transmitting the plurality of object active state signals simultaneously or non-simultaneously to a digital signal processing (DSP) device.

DETAILED DESCRIPTION OF THE DISCLOSED EMBODIMENTS

Figure 1A:
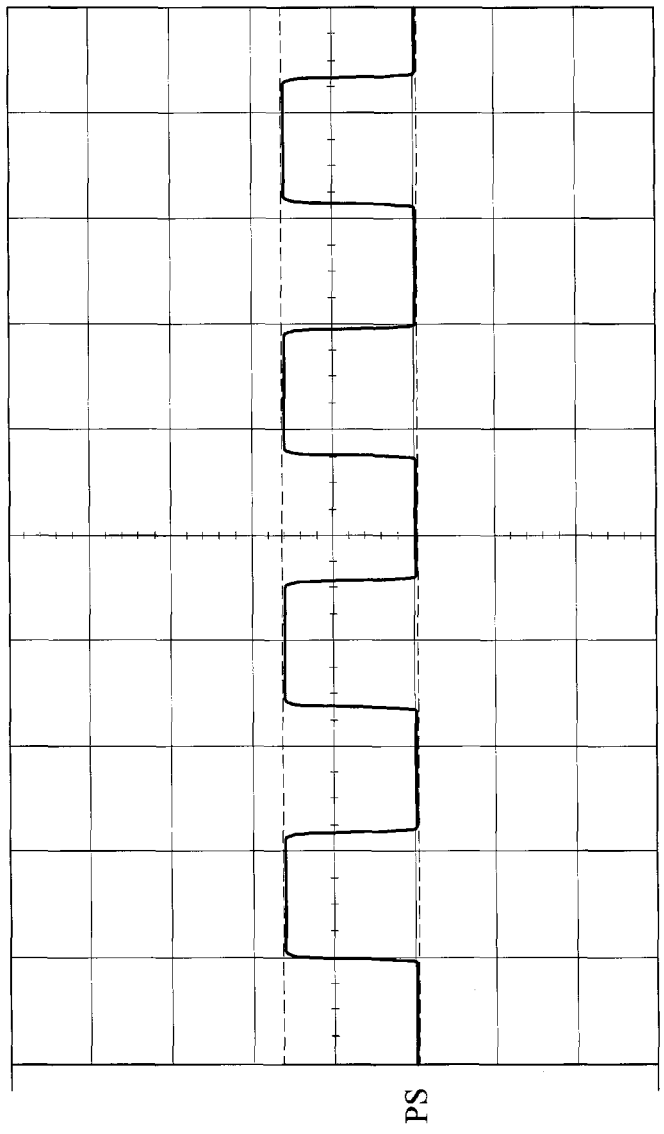
FIG. 1A, FIG. 1B, and FIG. 1C show schematic views of PWM signals PS, measuring signals with pulse overshoot and undershoot, and reflected signals RFS, respectively, according to an exemplary embodiment of the disclosure.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

The exemplary embodiments in the disclosure may provide a sensing technique that may apply a Pulse Width Modulation (PWM) technique to generate a series of measuring signals with pulse overshoot and undershoot, and may apply an asymmetric antenna module to transmit the measuring signals to a target object and receive a plurality of reflected signals reflected by the target object for the physiology measurements. A PWM signal may be, but not limited to a pulse with modulation signal generated by a PWM technique, or implemented by a pulse wave or a square wave with a fixed cycle.

The feature of the PWM is to modulate the transmission power in a time unit. The PWM signals may be applied to generate a series of measuring signals with pulse overshoot and undershoot. For example, when a jitter generator implemented by such as a NAND gate or an AND gate IC is applied, the PWM signals may be transformed into a series of measuring signals with pulse jitter. The asymmetric antenna module may include one or more transmitting antennae and a plurality of receiving antennae. The one or more transmitting antennae may transmit the measuring signals to a target object. The target object may be, but not limited to such as a human body or one of various objects that may reflect the measuring signals. The plurality of reflected signals are the measuring signals reflected by the target object.

Figure 1B:
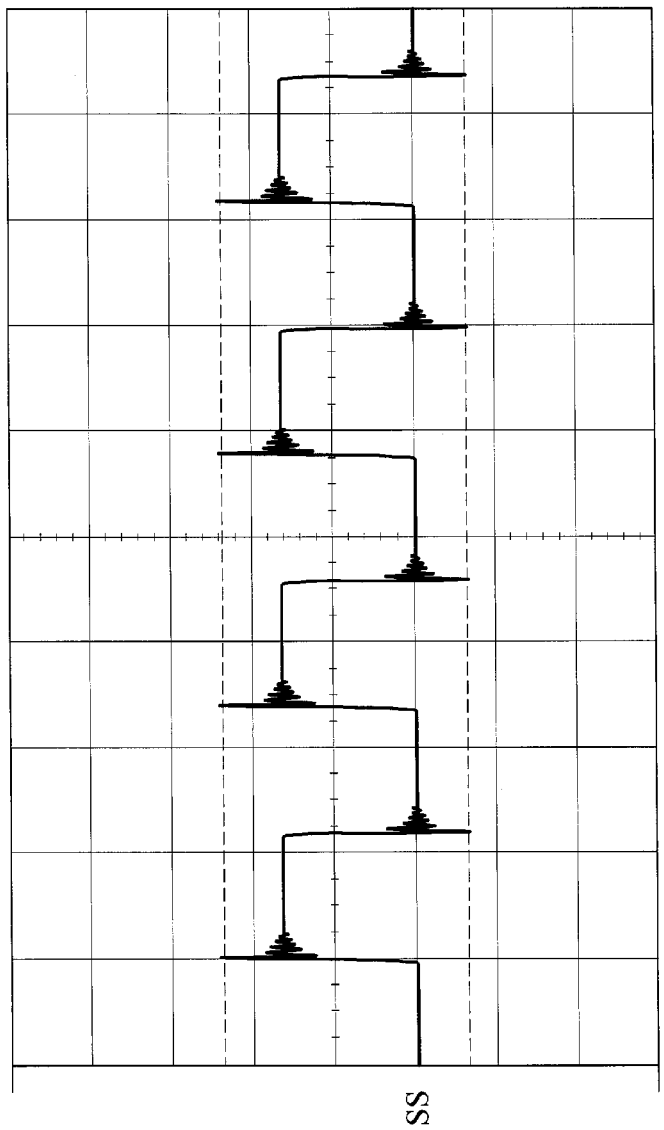
Figure 1C:
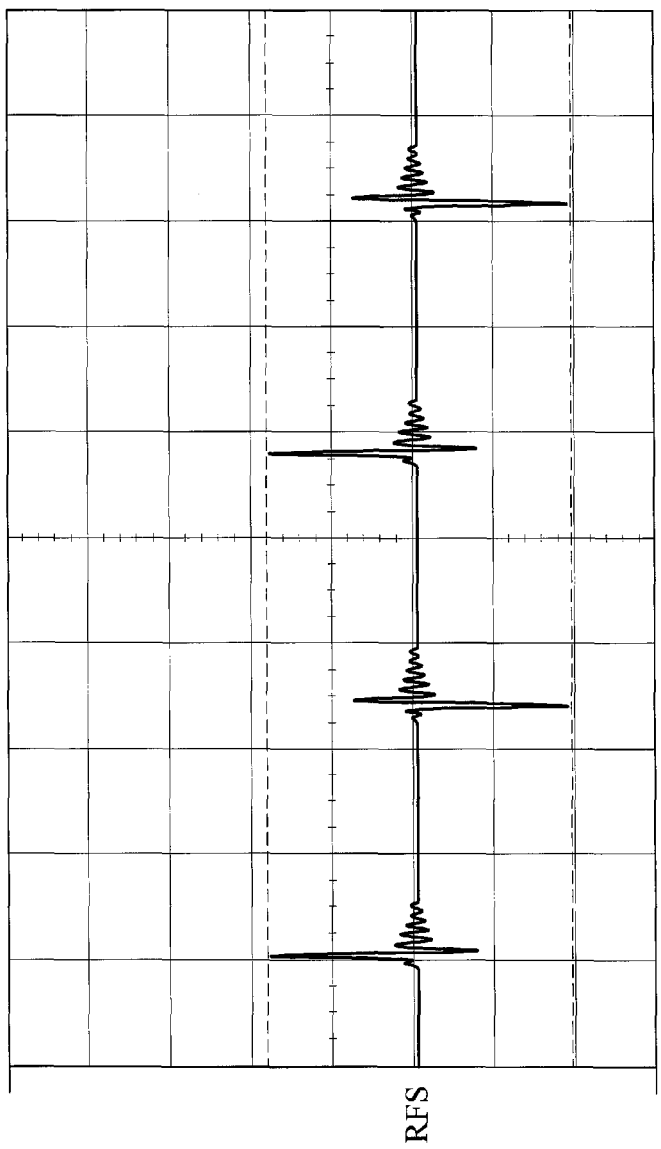

FIG. 1A, FIG. 1B, and FIG. 1C show schematic views of PWM signal PS, measuring signals with overshoot and undershoot waves, and reflected signal RFS, respectively, according to an exemplary embodiment of the disclosure. Referring to FIG. 1A, when a value of the PWM signal PS switches from a high value to a low value or switches from a low value to a high value, the PWM signal PS soon stabilizes because of the characteristics of the PWM technique itself. Referring to FIG. 1B, when a value of the measuring signal SS switches from a high value to a low value or switches from a low value to a high value, the measuring signal SS first undergoes a short shocking period. In this shocking period, the value of the measuring signal SS fluctuates and forms a waveform similar to a shock wave. After this shocking period, the measuring signal SS becomes stable. Referring to FIG. 1C, since the reflected signal RFS is generated by the measuring signal SS with the overshoot and undershoot pulses hitting the target object and then being reflected back, the reflected signal RFS that is generated by reflection also has a similar shocking period. After this shocking period, the reflected signal RFS becomes stable. In this way, the disclosure more accurately senses and judges the active state of the target object by analyzing the reflected signal that also has overshoot and undershoot pulses.

Figure 2:
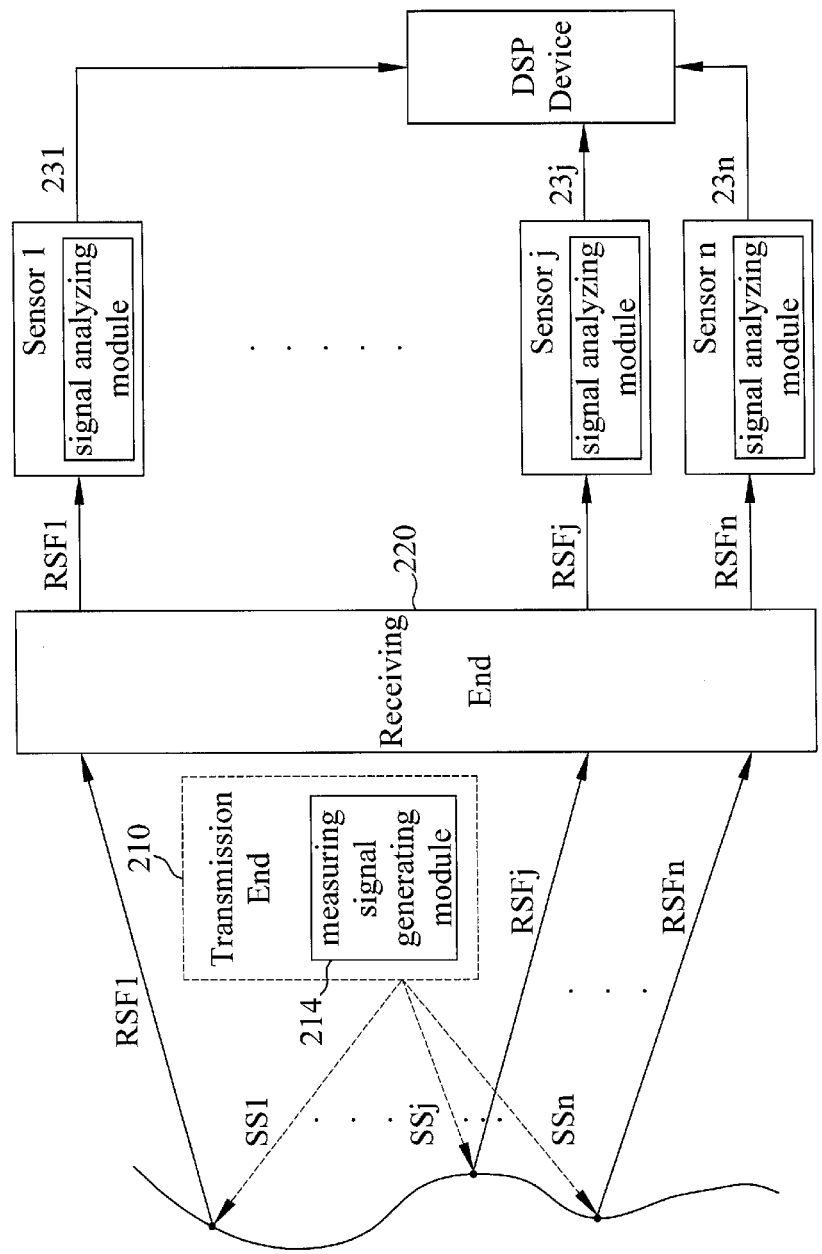
FIG. 2 shows a schematic view of a sensing architecture that applies a multi-system integration, according to one exemplary embodiment of the disclosure.

An exemplary architecture of this sensing technique may be implemented by applying a multi-system integration, as shown in FIG. 2. Wherein, the multi-system integration 200 may integrate a transmission end 210 and a receiving end 220, and a plurality of signal analyzing modules included in a plurality of sensors (such as sensor 1~sensor n), respectively. One or more measuring signals (such as SS1-SSn) generated by a measuring signal generating module 214 may be transmitted to a target object (not shown) from the transmission end 210, and one or more measuring signals reflected by the target object (i.e. reflected signals RFS1-RFSn) may be received by the receiving end 220 for further analyzing by the plurality of signal analyzing modules of the plurality of sensors. And then a plurality of object active state signals 231~23n outputted from the plurality of signal analyzing modules are transmitted simultaneously or non-simultaneously to a digital signal processing (DSP) device for subsequently processing.

Figure 3:
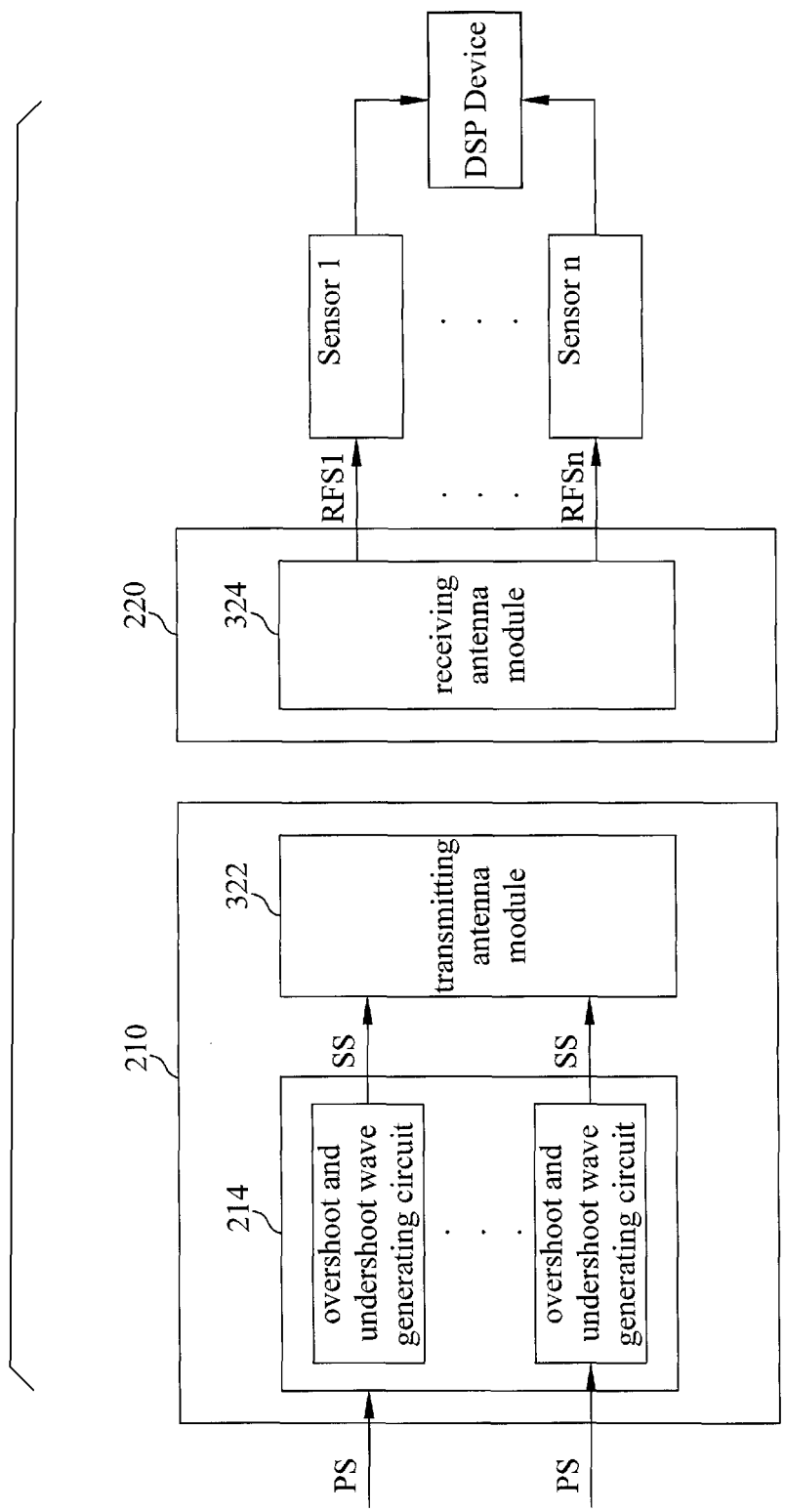
FIG. 3 shows a sensing system for physiology measurements, according to one exemplary embodiment.

With the exemplary architecture and according an exemplary embodiment, a sensing system for physiology measurements shown in FIG. 3 may comprise the transmission end 210 and the receiving end 220, and a plurality of signal analyzing modules included in a plurality of sensors such as sensor 1~sensor n. Wherein the transmission end 210 may further include a transmitting antenna module 322, and the measuring signal generating module 214 having one or more overshoot and undershoot wave generating circuits. The measuring signal generating module 214 may generate one or more measuring signals with overshoot and undershoot pulses, wherein each measuring signal SS is generated according to an inputted PWM signal PS. In other words, the measuring signal SS has a characteristics of a pulse wave, and overshoot and undershoot waves are also on the pulse wave. Each of the overshoot and undershoot wave generating circuits included in the measuring signal generating module 214 may generate a measuring signal SS. The transmitting antenna module 322 may include at least one transmitting antenna TX. Each transmitting antenna may transmit a measuring signal SS to a target object. The receiving end 220 may include a receiving antenna module 324 having a plurality of receiving antennae. Each of the plurality of receiving antennae may receive a RFS signal (a measuring signal reflected by the target object) for further analyzing by a signal analyzing module included in an associated sensor. After the analyzing, each object active state signal BS outputted from each signal analyzing module may be obtained, and then a plurality of object active state signals outputted from the plurality of signal analyzing modules are transmitted simultaneously or non-simultaneously to a DSP device for subsequently processing.

When the measuring signal SS is continuously transmitted by the transmitting antenna module 322 in the form of radiation, the reflected signal RFS is continuously reflected back once the measuring signal SS hits the target object, and then the reflected signal RFS is continuously received by the receiving antenna module 324. When an active state or a movement state of the target object changes, an angle and/or a hitting position at which the measuring signal SS hits the target object also changes, thereby resulting in a change in a frequency, a waveform or a receiving time of the reflected signal RFS received by the receiving antenna 324. In other words, according to the exemplary embodiments, real-time active state information of the target object may be effectively obtained by analyzing these reflected signals RFS.

In an application exemplar, the transmitting antenna module may be implemented by one transmitting antenna. In the application scenario, a plurality of reflected signals received by the plurality of receiving antennae may be a plurality of measuring signals that are transmitted, by the one transmitting antenna, to the target object and reflected by the target object. In another application exemplar, the transmitting antenna module may be implemented by a plurality of transmitting antennae, and a plurality of reflected signals received by the plurality of receiving antennae may be a plurality of measuring signals that are transmitted respectively by the plurality of transmitting antennae to the target object and reflected by the target object.

In an application exemplar, the measuring signal generating module 214 may be implemented by a plurality of overshoot and undershoot wave generating circuits with the each overshoot and undershoot wave generating circuit being coupled to an associated signal analyzing module of the plurality of sensors for generating the measuring signal used by the associated sensor, respectively. In another application exemplar, the measuring signal generating module may be implemented by one overshoot and undershoot wave generating circuit coupled to the plurality of signal analyzing modules for generating a plurality of measuring signals according to a series of inputted PWM signals, and then the transmitting antenna module transmits the plurality of measuring signals to the target object.

Figure 4:
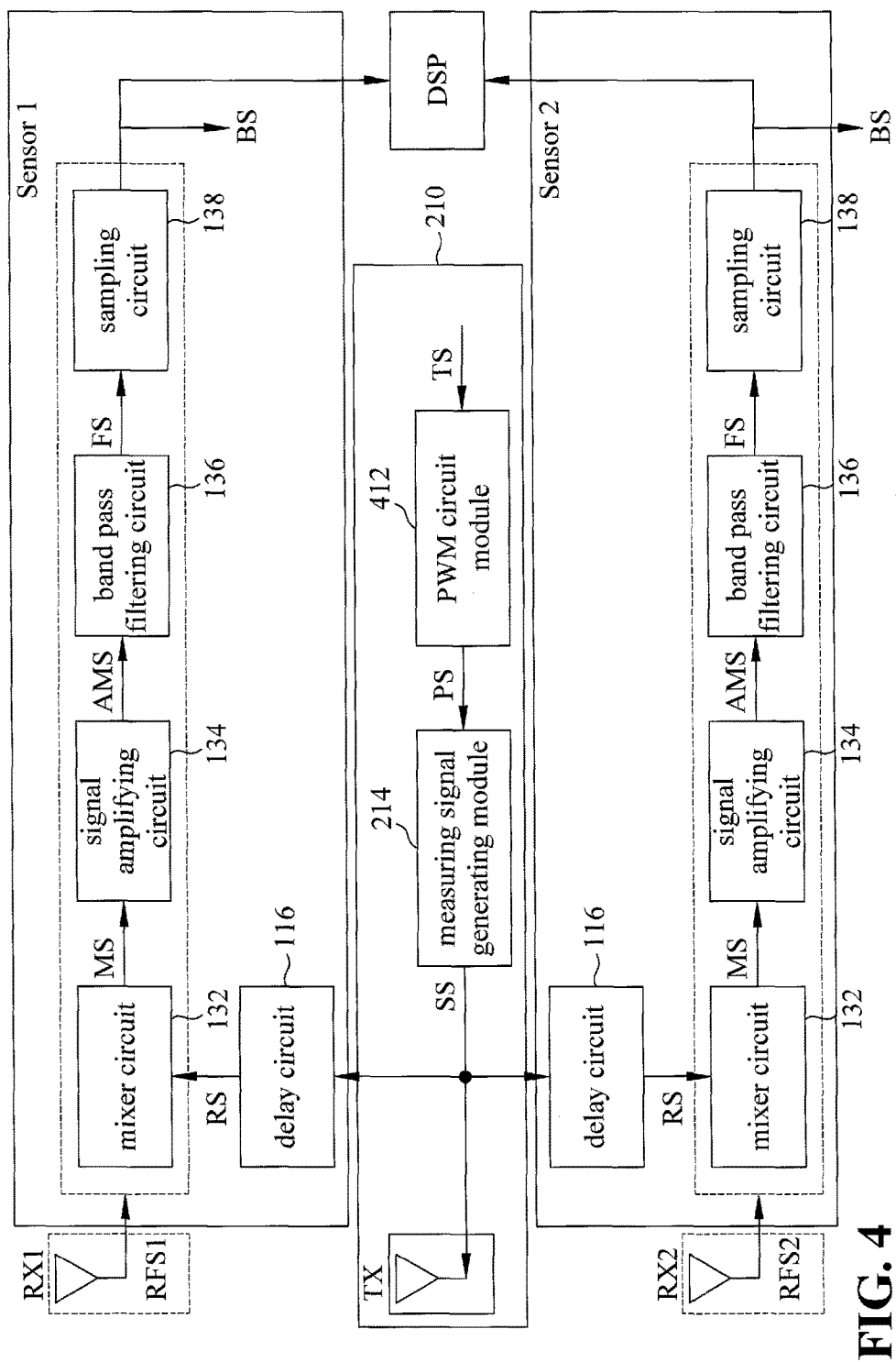
FIG. 4 shows a system structure for the sensing system for physiology measurements, according to an exemplary embodiment.

Take two sensors (referred as Sensor 1 and Sensor 2) as an exemplar. FIG. 4 shows a system structure for the sensing system for physiology measurements, according to an exemplary embodiment. As shown in FIG. 4, the transmission end 210 may further include a PWM circuit module 412 coupled to the measuring signal generating module 214 to generate the PWM signal PS according to a clock signal TS, thereby providing the PWM signal PS to the measuring signal generating module 214. At the receiving end 220, each sensor may receive a reflected signal RFS from a receiving antenna (referred as RX1 and RX2 for Sensor 1 and Sensor 2, respectively), and include a delay circuit 116 and a signal analyzing module. The signal analyzing module may further include a mixer circuit 132, a signal amplifying circuit 134, a band pass filtering circuit 136, and a sampling circuit 138. The delay circuit 116 is coupled to the measuring signal generating module 214 to generate a reference signal RS according to the measuring signal SS. The mixer circuit 132 is coupled to the receiving antenna module 324 and the delay circuit 116 to mix the reflected signal RFS and the reference signal RS to be a mixing signal MS. The signal amplifying circuit 134 is coupled to the mixer circuit 132 to amplify the mixing signal MS to be an amplified mixing signal AMS. The band pass filtering circuit 136 is coupled to the signal amplifying circuit 134 to perform a filtering operation on the amplified mixing signal AMS to generate a filtered signal FS. The sampling circuit 138 is coupled to the band pass filtering circuit 136 to perform a sampling operation on the filtered signal FS, thereby obtaining the object active state signal BS. The signal amplifying circuit 134, the band pass filtering circuit 136 and the sampling circuit 138 may all be adjustable according to practical or design requirements. These circuits are not the focus of the disclosure, and the detailed descriptions thereof are omitted herein.

Figure 5:
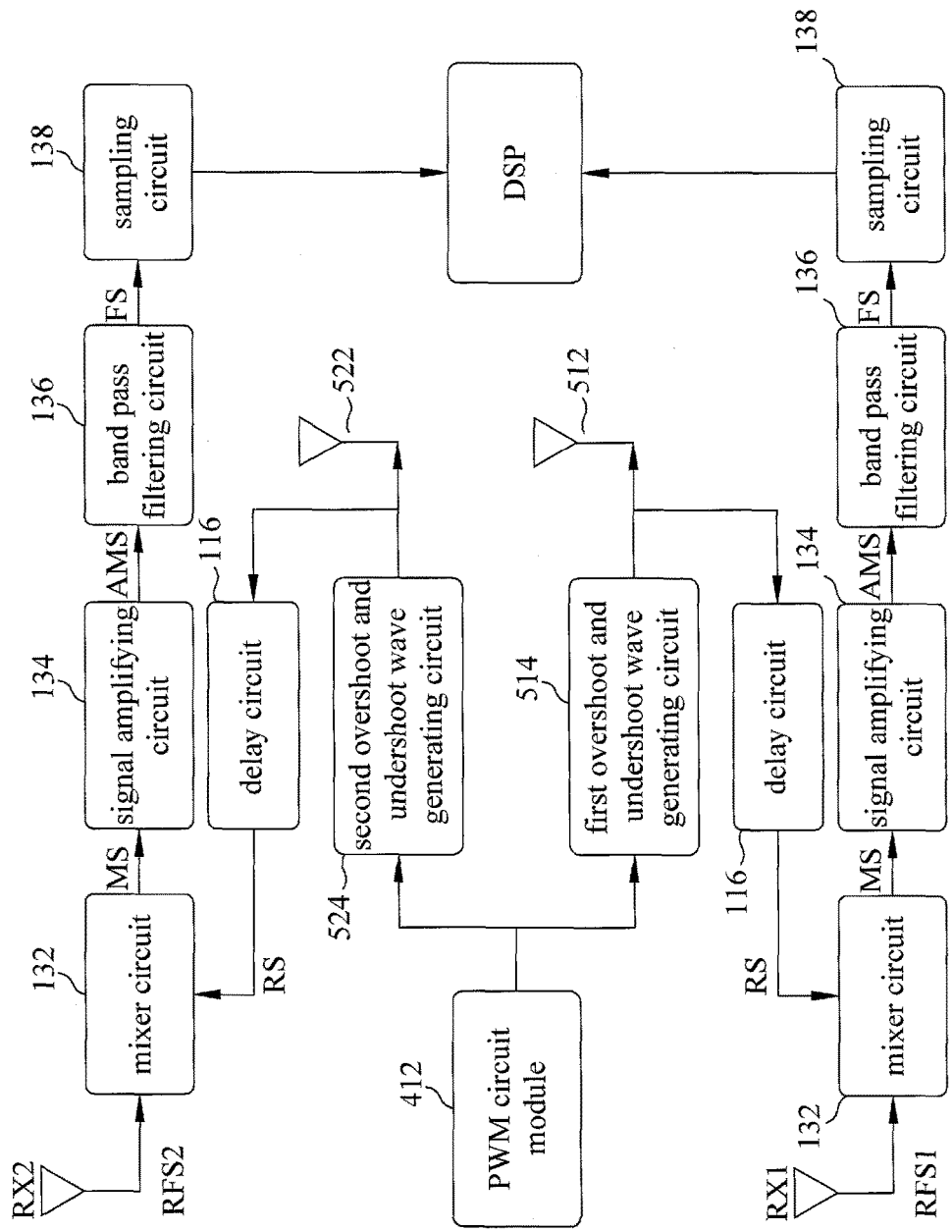
FIG. 5 shows a schematic view illustrating the measuring signal generating module and the transmitting antenna module are extended to become two sets, according to one exemplary embodiment.

According to an exemplary embodiment, the measuring signal generating module 214 and the transmitting antenna module 322 may be extended to become n sets, with each set including an overshoot and undershoot wave generating circuit and a transmitting antenna and being provided to each sensor of the sensor 1~sensor n, respectively, for use. Take two sensors, such as sensor 1 and sensor 2, as an exemplar. As shown in FIG. 5, the measuring signal generating module 214 may include a first overshoot and undershoot wave generating circuit 514 and a second overshoot and undershoot wave generating circuit 524. The transmitting antenna module 322 may include a first transmitting antenna 512 and a second transmitting antenna 522. A first set formed by the first overshoot and undershoot wave generating circuit 514 and the first transmitting antenna 512 may be used by the sensor 1, and a second set formed by the second overshoot and undershoot wave generating circuit 524 and the second transmitting antenna 522 may be used by the sensor 2, respectively, for use. In other words, each sensor uses respective overshoot and undershoot wave generating circuit and respective transmitting antenna, according to the exemplary embodiment. In this exemplar, the sensor 1 and the sensor 2 share with the PWM circuit module 412 that provides the inputted PWM signals to both of the first overshoot and undershoot wave generating circuit 514 and the second overshoot and undershoot wave generating circuit 524.

Figure 6:
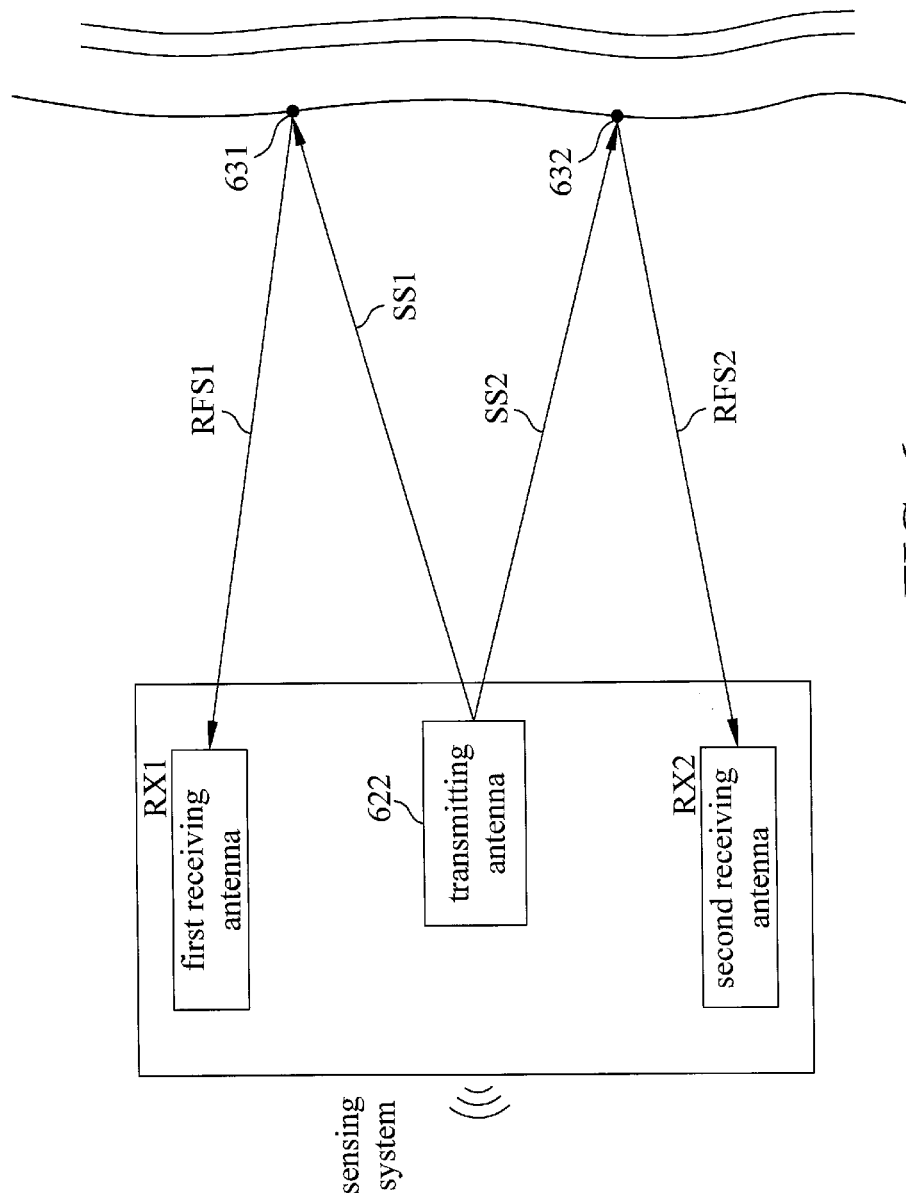
FIG. 6 shows a schematic view illustrating an application scenario of a transmitting antenna sharing by two receiving antennae in a sensing system, according to an exemplary embodiment.

According to another exemplary embodiment, the plurality of sensors may share with the transmitting antennae in the transmitting antenna module 322. FIG. 6 shows a schematic view illustrating an application scenario of a transmitting antenna sharing by two receiving antennae in a sensing system, according to an exemplary embodiment. Referring to the exemplar in FIG. 6, in the sensing system, there are two receiving antennae referred as a first receiving antenna RX1 and a second receiving antenna RX2 at the receiving end, and one transmitting antenna 622 at the transmission end. When the measuring signal SS is continuously transmitted by the transmitting antenna 622 in the form of radiation, the reflected signal RFS is continuously reflected back once the measuring signal SS hits a measuring point of a target object (not shown), and then the reflected signal RFS is continuously received by one of the two receiving antennae. For example, when a first measuring signal SS1 is transmitted by the transmitting antenna 622, a first reflected signal RFS1 is reflected back once the measuring signal SS1 hits a first measuring point 631 of the target object, and then the first reflected signal RFS1 is received by the first receiving antenna RX1. Similarly, when a second measuring signal SS2 is transmitted by the transmitting antenna 622, a second reflected signal RFS2 is reflected back once the measuring signal SS2 hits a second measuring point 632 of the target object, and then the second reflected signal RFS2 is received by the second receiving antenna RX2. The first receiving antenna and the second antenna could be implemented by more than one antennae.

Figure 7:
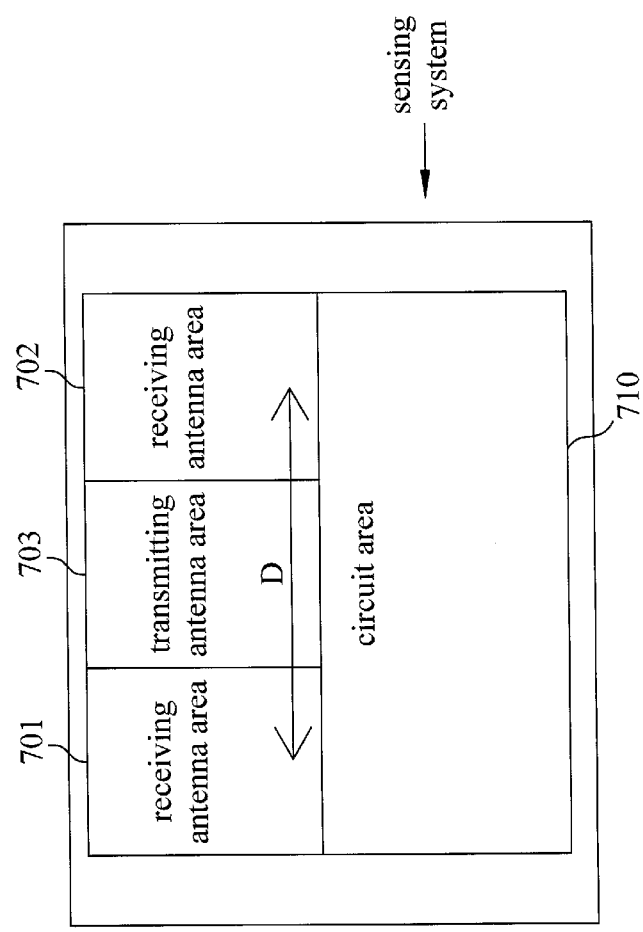
FIG. 7 shows a schematic view illustrating a physical configuration of the sensing system for physiology measurements, according to an exemplary embodiment.
Figure 8:
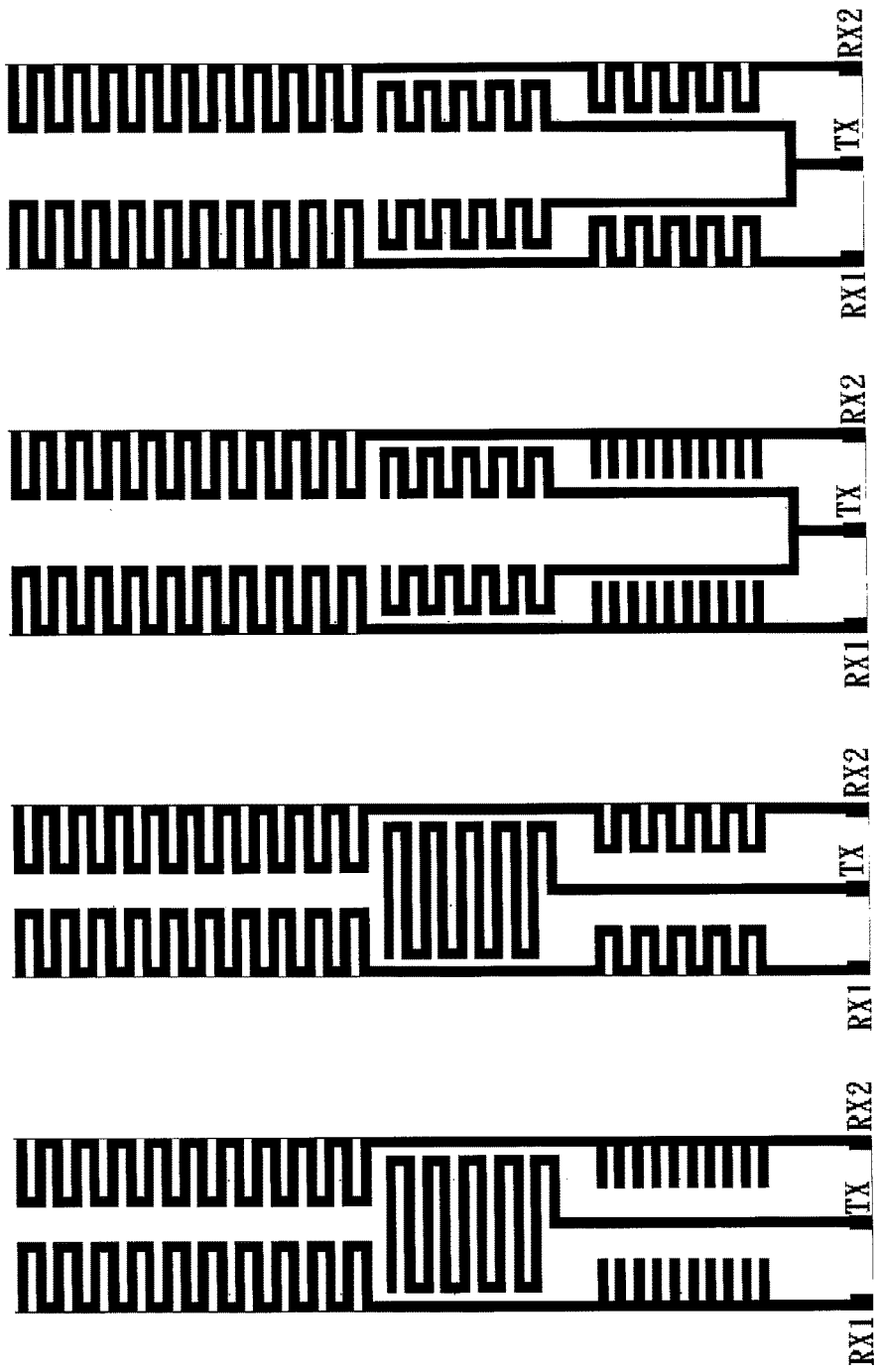
FIG. 8A~FIG. 8D shows four exemplary kinds of an asymmetric comb-shaped antenna module used as the transmitting and receiving antennae, according to exemplary embodiments.

FIG. 7 shows a schematic view illustrating a physical configuration of the sensing system for physiology measurements, according to an exemplary embodiment. Referring to FIG. 7, the sensing system may be configured into a circuit area 710, and a plurality of antenna areas, such as two receiving antenna areas 701 and 702 and a transmitting antenna area 703. The measuring signal generating module 214 and the plurality of signal analyzing modules may be configured in the circuit area 710. The plurality of receiving antennae may be distributed in a plurality of receiving antenna areas surrounding a transmitting antenna area. Take two sensors as an exemplar. Two receiving antennae may be configured in two receiving antenna areas 701 and 702, respectively. The transmitting antenna module 322 may be configured between the receiving antenna areas 701 and 702, where D is a distance between the two receiving antennae. In other words, the sensing system for physiology measurements may be further configured into a circuit area containing the measuring signal generating module 214 and the plurality of signal analyzing modules, and a plurality of antenna areas containing the plurality of receiving antennae and the transmitting antenna module 322 surrounded by the plurality of receiving antennae.

Figure 9:
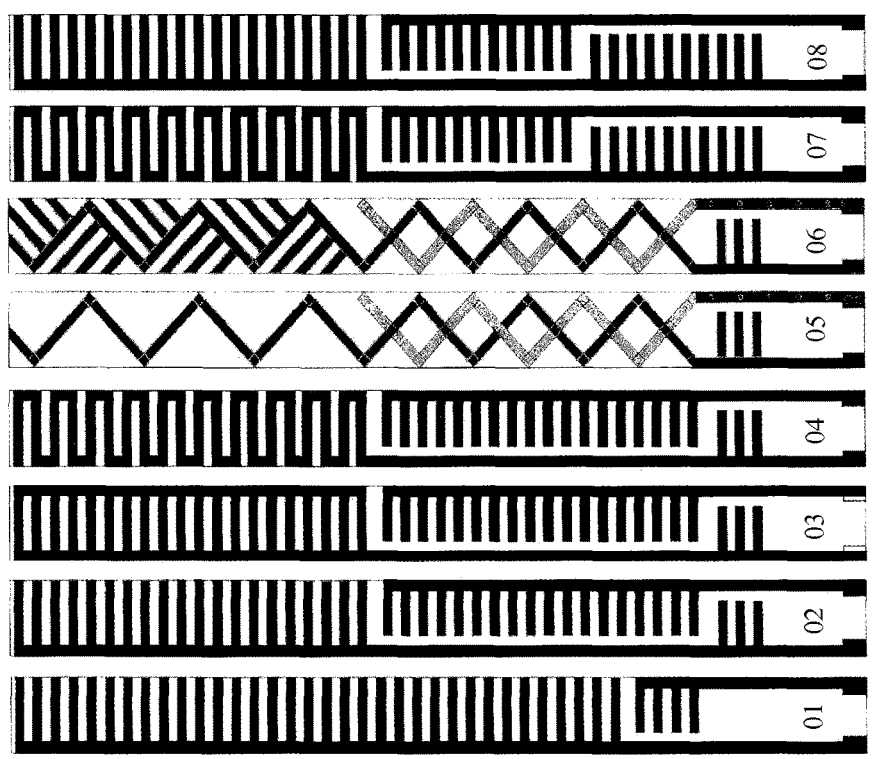
FIG. 9 shows various variations regarding the asymmetric comb-shaped antenna module, according to the exemplary embodiments.

The following describes the antenna design. For the transmitting antenna in the transmitting antenna module and the receiving antennae at the receiving end, an asymmetric comb-shaped antenna module may be used as the transmitting and receiving antennae. FIG. 8A~FIG. 8D shows four exemplary types of an asymmetric comb-shaped antenna module used as the transmitting and receiving antennae, according to exemplary embodiments. For each exemplary asymmetric comb-shaped antenna module, assume that there are two receiving antennae at the receiving end, and one transmitting antenna in the transmitting antenna module. FIG. 9 further shows various variations regarding the asymmetric comb-shaped antenna module, according to the exemplary embodiments. According to the exemplary embodiments in the disclosure, any antenna combinations of these various variations regarding the asymmetric comb-shaped antenna module shown in FIG. 9 may be used as the transmitting and receiving antennae. In other words, the at least one transmitting antenna of the transmitting antenna module and the plurality of receiving antennae at the receiving end may respectively have a comb-shaped structure.

Figure 10:
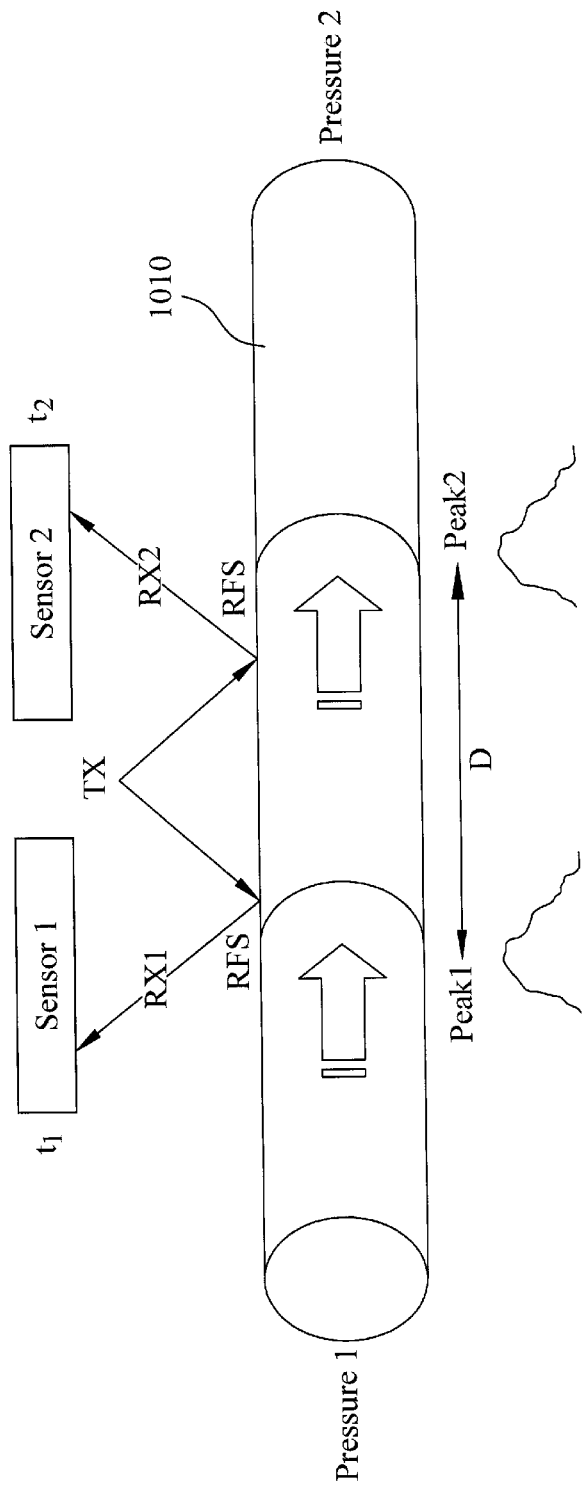
FIG. 10 shows a schematic view illustrating an application relation between physical circuits of the sensing system and vein, according to an exemplary embodiment.

According to the exemplary embodiments, the sensing system may be applied to measure pressures of veins such as but not be limited to the systolic and diastolic blood pressures of an artery. FIG. 10 shows a schematic view illustrating an application relation between physical circuits of the sensing system and vein of a target object such as a human body, according to an exemplary embodiment. In the exemplary embodiment of FIG. 10, the physical circuits of the sensing system may uses two sensors such as sensor 1 and sensor 2, and two receiving antennae such as RX1 and RX2 and at least one transmitting antenna such as TX to measure pressure 1 and pressure 2 of vein 1010 such as the systolic and diastolic blood pressures of the artery. The measuring signal generating module of the sensing system may generate a first measuring signal and a second measuring signal according to an inputted Pulse Width Modulation (PWM) signal. The at least one transmitting antenna TX transmits the first and the second measuring signals to the vein 1010 for being used by the sensor 1 and the sensor 2, respectively. Each of the two receiving antennae RX1 and RX2 may respectively receive a reflected signal RFS reflected by the vein 1010 for being used and analyzed by the sensor 1 and the sensor 2, respectively. While a time difference $t_2$ is larger than a time difference $t_1$ (i.e. receiving time of a first scattered pulse signal—emitting time of a first radiated pulse signal), a pulse peak would occur, wherein the time difference $t_1$ is a previous time difference to the time difference $t_2$, and Peak 1 corresponds to the pulse peak received by the RX1 for sensor 1, Peak 2 corresponds to the pulse peak received by the RX2 for sensor 2.

Figure 11:
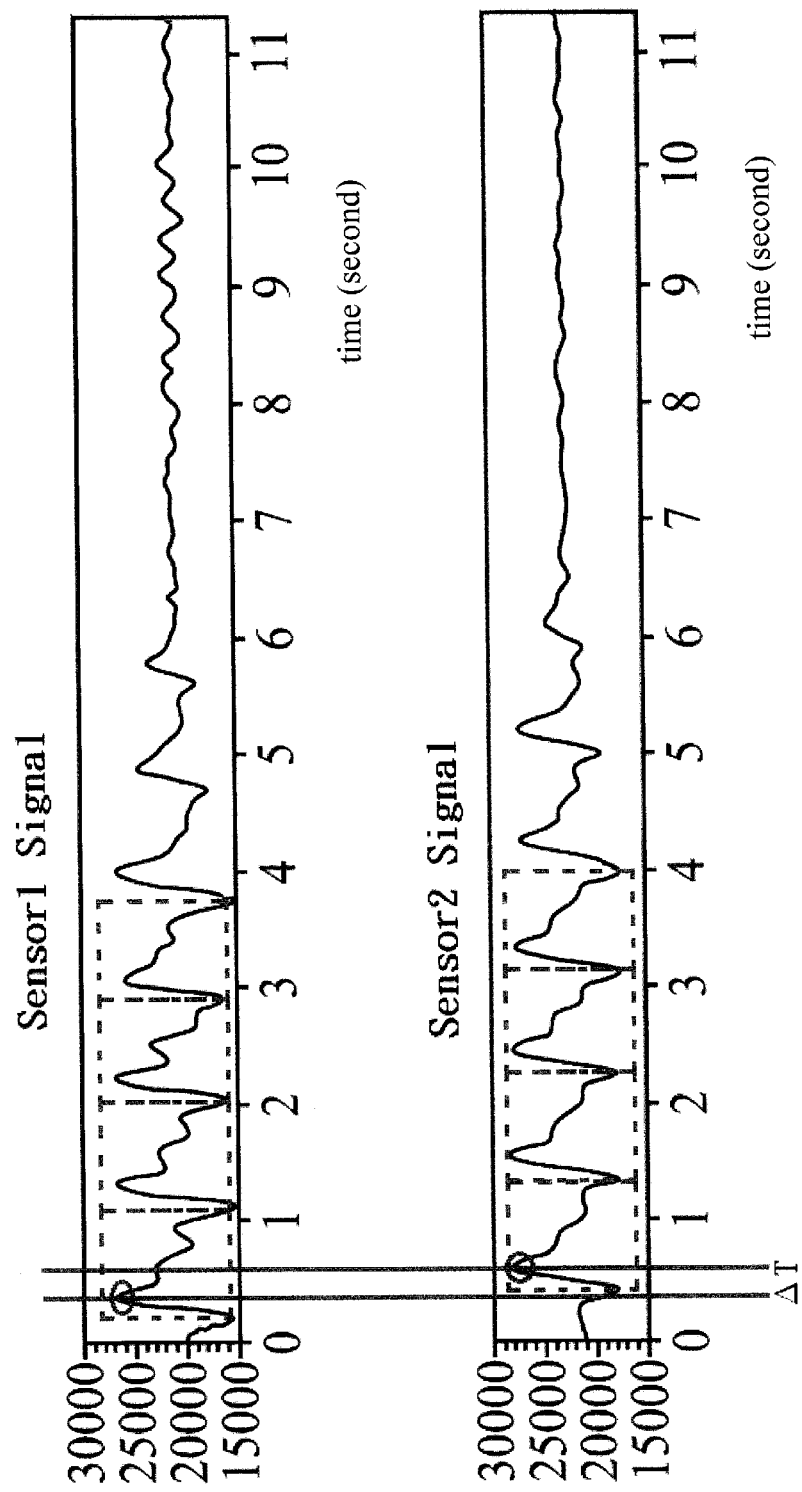
FIG. 11 shows signals received by sensor 1 and sensor 2 in FIG. 10 after digital sampling, according to an exemplary embodiment.

FIG. 11 further shows signals received by sensor 1 and sensor 2 after digital sampling, according to an exemplary embodiment. Referring to FIG. 11, as may be seen, a time lapse $\Delta T$, i.e. a pulse time difference of the first pulse peak and the second pulse peak, exists between the signals received by sensor 1 and sensor 2 because the pulse experiences lagging during transmission. In other words, the time lapse $\Delta T$ may be obtained through two different generating times of two different pulse peaks received by two different antennae, as shown in the following formula for the case of FIG. 11:

$\Delta T$=generating time of the second pulse peak–generating time of the first pulse peak.

Figure 12:
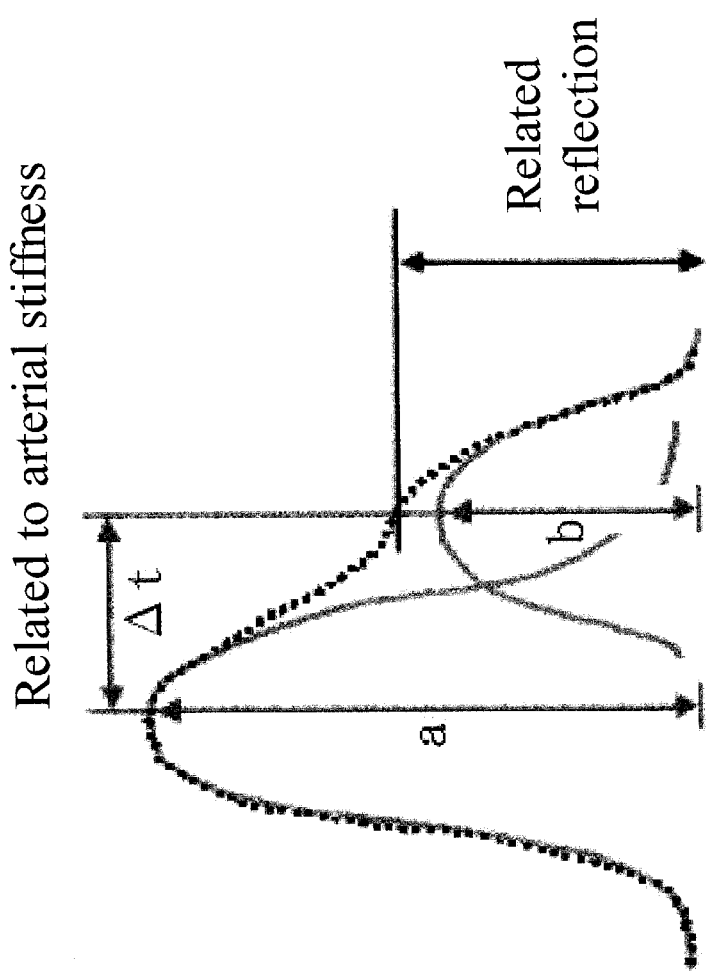
FIG. 12 shows obtained waveforms being accumulated in the dotted blocks in FIG. 11, according to one exemplary embodiment.

The following uses blood pressure measurement as an exemplar to describe the computation of the systolic and diastolic blood pressures. In processing signal, the receiving time $t_1$ and $t_2$ of the pulses are used to calculate the pulse wave velocity (PWV). For example, the PWV may be expressed as a function of a distance D between two different receiving antennae, and a time difference of two signals received by different sensors, respectively. One of examples is, PWV=D/$\Delta T$. In other words, the time lapse $\Delta T$ may be used as the time difference. In the DSP, the waveform in the dotted blocks shown in FIG. 11 may be accumulated to obtain the waveform in the FIG. 12. According to the waveform transmission and reflection theory, the pressure sensing waveform obtained by a wrist may be divided into two parts, wherein the first part of the waveform is the pulse reaching the wrist by following the path of a main artery (i.e. the waveform with a height a in the FIG. 12); and the second part of the waveform is the pulse reaching the micro-vascular of a hand and then reflected (i.e. the waveform with a height b in the FIG. 12) back to the wrist.

Figure 13:
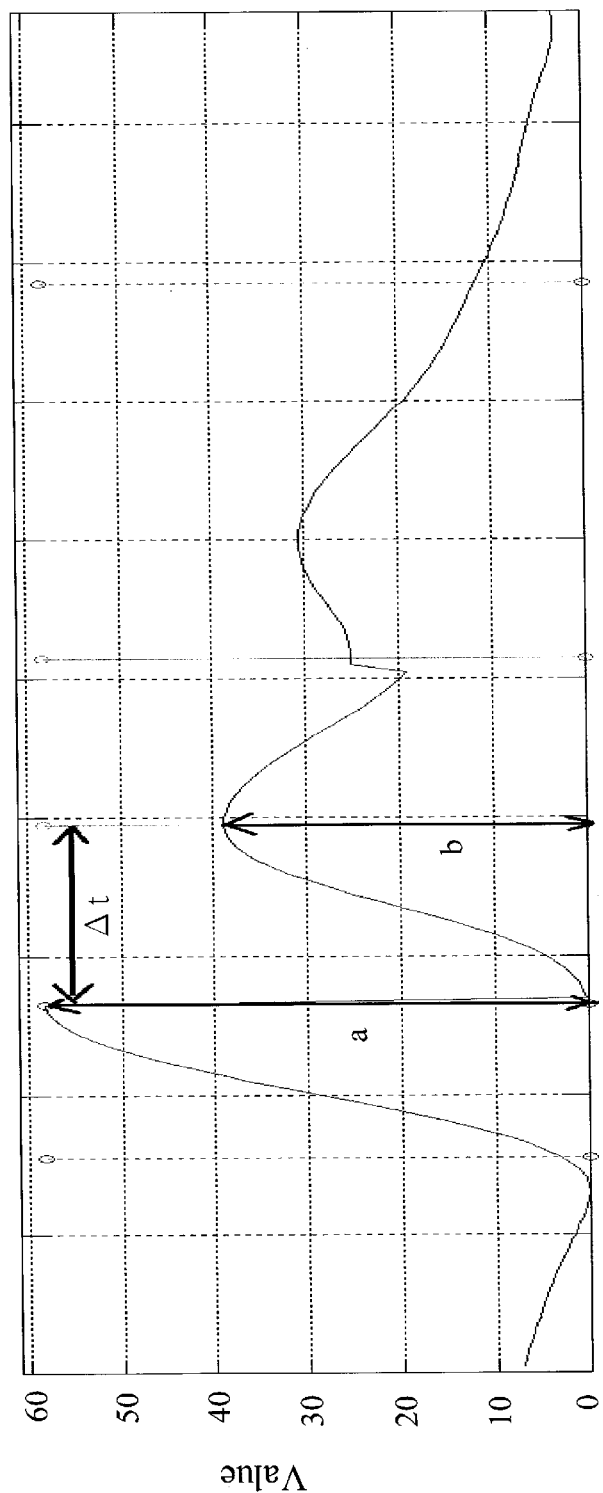
FIG. 13 shows obtained information by accumulating and analyzing the waveforms received by the sensor 1 and the sensor 2 during the diginal signal processing, according to one exemplary embodiment.

The time lapse $\Delta t$ between the main wave and the reflected wave (vascular stiffness index SI=$\Delta t$) and the height ratio of the main wave and the reflected wave (vascular reflection index RI=a/b) may be used to compute the extent of hardening of the artery, and may also be used to detect the blood pressure. Based on the above method, according to an exemplary embodiment, the waveforms received by the sensor 1 and the sensor 2 are accumulated and analyzed during the digital signal processing, and then the information shown in FIG. 13 is obtained. In other words, applying the waveform transmission and reflection theory such as Bernoulli's theory, a linear relation between the blood pressure (BP) and pulse wave velocity (PWV) may be expressed as $$BP=a \times PWV+b$$

wherein a and b are vascular parameters calculated by the original pulse signal measured by a sensor, and the pulse wave velocity (PWV) is a measure of a first measure point and a second measure point of a target object such as an artery; a and b are vascular parameters calculated by the original pulse signal measured by the sensor.

Through further analysis on the measured wave and vascular parameter analysis, the relation among the vascular stiffness index (SI), vascular reflection index (RI) and heart rate (HR) may be computed, and the blood pressure (BP) is a function of the pulse wave velocity (PWV), vascular stiffness index (SI), vascular reflection index (RI) and heart rate (HR), i.e. BP=F(PWV, SI, RI, HR). Therefore, the aforementioned method may detect the blood pressure such as the systolic and diastolic blood pressures, through combining the sensing system of the disclosure and the blood flow velocity algorithm. And, the systolic blood pressure $BP_{Sys}$ and the diastolic blood pressure $BP_{Dia}$ of an artery may be obtained by using the algoithm including the following formula.

$$BP_{Sys}=a_1 \times PWV+b_1$$

$$BP_{Dia}=a_2 \times PWV+b_2$$

wherein the pulse wave velocity (PWV) may be calculated by the formula PWV=D/$\Delta T$, $a_1$ and $b_1$ are vascular parameters calculated by the original pulse signal measured by the sensor 1, and $a_2$ and $b_2$ are vascular parameters calculated by the original pulse signal measured by the sensor 2. Therefore, this may improve the precision of the transformation from the PWV to the presure measurements, and the feasibility and practicality will be significantly effective to the users.

If the regression analysis and comparison are performed on the blood pressure measurements obtained by the standard blood pressure meter with a cuff, obtained blood pressure equations are:

systolic blood pressure SBP=$0.00022318X^2$+ $0.21107X$+$90.381$, diastolic blood pressure DBP=0.00044459$X^2$+ 0.29295$X$+38.33

And, the cuff needs to be inflated and deflated for indirectly measuring non-continuous blood pressure. When measuring continuous blood pressure, the cuff needs to be setup correctly and be inflated and deflated repetitively. In one exemplary embodiment, $$X = \frac{C}{\left[\frac{SI}{PWV} \times \frac{1}{\Delta T} \times \ln\left(\sqrt{\frac{HR \times SI}{RI}}\right)\right]}$$

wherein C is a constant.

Accordingly, the sensing system may also be applied to measure pressures, such as blood pressure measurement of the main arteries of the chest, blood pressure measurement of the carotid arteries of the neck (also applicable to brain pressure measurement), blood pressure measurement of the peripheral vascular, and so on. The sensing system may further comprise a signal processing device including a wireless module, and a microcontroller to calculate pressures. The microcontroller may have a calculation unit which has an algorithm such as the aforementioned blood flow velocity algorithm. The signal processing device may use the wireless module to communicate with the plurality of sensors via a wireless protocol. The wireless protocol may be, but not limited to a Bluetooth protocol. The calculation unit may uses the algorithm to calculate the pressures such as the aforementioned blood pressures. The algorithm may include the aforementioned relation formula between the blood pressure (BP) and pulse wave velocity (PWV).

Figure 14:
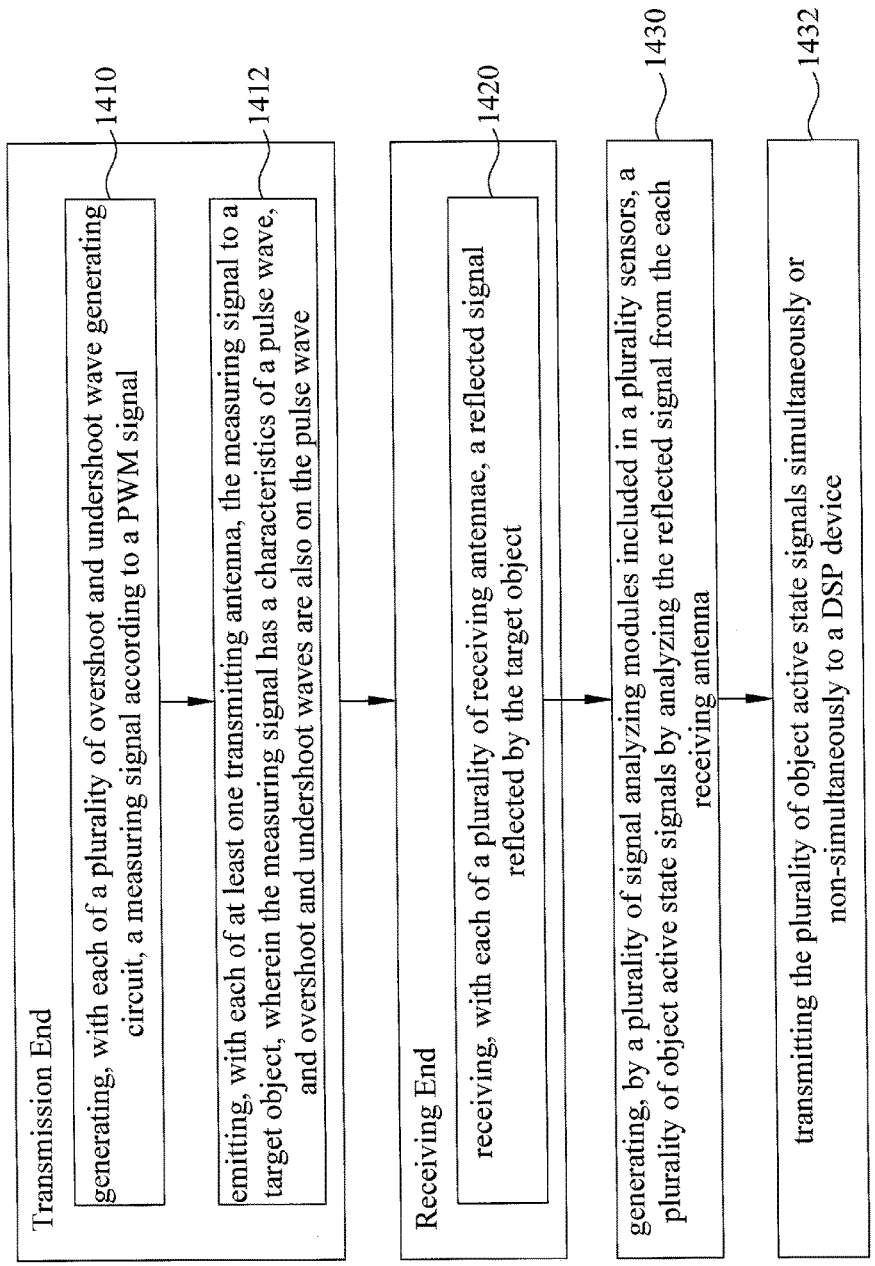
FIG. 14 shows a sensing method for physiology measurements, according to one exemplary embodiment.

FIG. 14 shows a sensing method for physiology measurements, according to one exemplary embodiment. Referring to FIG. 14, the sensing method for physiology measurements may comprise: at a transmission end, generating, with each of a plurality of overshoot and undershoot wave generating circuit, a measuring signal according to a Width Modulation (PWM) signal (step 1410), and emitting, with each of at least one transmitting antenna, the measuring signal to a target object, wherein the measuring signal has a characteristics of a pulse wave, and overshoot and undershoot waves are also on the pulse wave (step 1412); at a receiving end, receiving, with each of a plurality of receiving antennae, a reflected signal reflected by the target object (step 1420); and generating, by a plurality of signal analyzing modules respectively included in a plurality sensors, a plurality of object active state signals by analyzing the reflected signal from the each receiving antenna (step 1430), and transmitting the plurality of object active state signals simultaneously or non-simultaneously to a digital signal processing (DSP) device (step 1432).

As aforementioned, the measuring signal may be generated by generating the pulse width modulation signal according to a clock signal, and modulating the pulse width modulation signal to be the measuring signal with the overshoot and undershoot pulses by means of a digital signal processing. As shown in the examples of FIG. 8A~FIG. 8D and FIG. 9, an asymmetric comb-shaped antenna module, or various variations regarding the asymmetric comb-shaped antenna module may be used as the at least one transmitting antenna at the transmission end and the plurality of receiving antennae at the receiving end. The detailed descriptions thereof are omitted herein.

The sensing method may also be applied to measure pressures of the target object, such as but not be limited to the systolic blood pressure $BP_{Sys}$ and the diastolic blood pressure $BP_{Dia}$ of an artery, as described in FIG. 10. In the digital signal processing, the calculation of a pressure measurement of the target object may include: calculating a pulse time difference of a first pulse peak and a second pulse peak, wherein the first pulse peak and the second pulse peak are received by two different antennae of the plurality of antennae; calculating a pulse wave velocity (PWV) by using the pulse time difference and a distance between the first pulse peak and the second pulse peak; calculating each pressure of one or more pressures, by expressing a linear relation between the pressure and the pulse wave velocity. As shown in the aforementioned examples and descriptions, the pressure measurement may be chosen from one or more combinations of a blood pressure measurement of a plurality of main arteries of a chest, a blood pressure measurement of a plurality of carotid arteries of a neck, a brain pressure measurement, a blood pressure measurement of a peripheral vascular. The detailed descriptions thereof are omitted herein.

According to another exemplary embodiment of the present disclosure, there is provided a chip for physiology measurements. The chip for physiology measurements may integrate at least one transmitting antenna, a plurality of receiving antennae, and an integrated circuit. The integrated circuit may further include one or more overshoot and undershoot wave generating circuits and a plurality of sensors. Each overshoot and undershoot wave generating circuit and each circuit in each sensor are configured to perform their associated acts described in the above embodiments. An exemplary physical configuration of the chip for physiology measurements may be configured into a circuit area and a plurality of antenna areas, similar to that of the FIG. 7. In other words, the sensing system for physiology measurements may be implemented by a chip, and the chip may integrate at least one transmitting antenna, a plurality of receiving antennae, and an integrated circuit having one or more overshoot and undershoot wave generating circuits and a plurality of sensors.

The exemplary embodiments have at least following features: (1) The sensing technique for physiology measurements, such as for blood pressure, may be realized with PWM, overshoot and downshoot pulses, and an asymmetric comb-shaped antenna module or various variations thereof; (2) the outputs, such as the plurality of object active state signals from the sensors are transmitted simultaneously or non-simultaneously to a digital signal processor for further processing and/or analyzing; (3) the measuring signal generating module and the transmitting antenna module may be extended to become n sets, with each set including an overshoot and undershoot wave generating circuit and a transmitting antenna and being provided to each sensor of the n sensors, respectively; and (4) each pressure of one or more pressures may be calculated by expressing a linear relation between the pressure and a pulse wave velocity.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:
1. A sensing system for physiology measurements of blood pressure or pulse wave velocity, comprising:

a transmission end including a measuring signal generating module having one or more overshoot and undershoot wave generating circuits with each overshoot and undershoot wave generating circuit generating a measuring signal according to a Pulse Width Modulation (PWM) signal, and a transmitting antenna module having at least one transmitting antenna with each transmitting antenna emitting the measuring signal to a target object, wherein the measuring signal has a characteristics of a pulse wave, and overshoot and undershoot waves are also on the pulse wave;

a receiving end having a plurality of receiving antennae with each receiving antenna receiving a reflected signal reflected by the target object; and a plurality of signal analyzing modules included in a plurality of sensors to generate a plurality of object active state signals by analyzing the reflected signal from the each receiving antenna, then transmit the plurality of object active state signals simultaneously or non-simultaneously to a digital signal processor, wherein the measuring signal is in a form of a radiation capable of being reflected from a physical body having blood flowing therein.

2. The sensing system as claimed in claim 1, wherein the transmitting antenna module is implemented by one transmitting antenna, and a plurality of reflected signals received by the plurality of receiving antennae are a plurality of measuring signals that are transmitted by said one transmitting antenna to the target object and reflected by the target object.

3. The sensing system as claimed in claim 1, wherein the transmitting antenna module is implemented by a plurality of transmitting antennae, and a plurality of reflected signals received by the plurality of receiving antennae are a plurality of measuring signals that are transmitted respectively by said plurality of transmitting antennae to the target object and reflected by the target object.

4. The sensing system as claimed in claim 1, wherein the measuring signal generating module is implemented by a plurality of overshoot and undershoot wave generating circuits with the each overshoot and undershoot wave generating circuit being coupled to an associated sensor of the plurality of sensors for generating the measuring signal used by the associated sensor, respectively.

5. The sensing system as claimed in claim 1, wherein the measuring signal generating module is implemented by one overshoot and undershoot wave generating circuit coupled to the plurality of sensors for generating a plurality of measuring signals according to a series of inputted PWM signals, and then the transmitting antenna module transmits the plurality of measuring signals to the target object.

6. The sensing system as claimed in claim 1, wherein the transmission end further include a PWM circuit module coupled to the measuring signal generating module to generate the PWM signal according to a clock signal.

7. The sensing system as claimed in claim 1, wherein the sensing system is further configured into a circuit area containing the measuring signal generating module and the plurality of sensors, and a plurality of antenna areas containing the plurality of receiving antennae and the transmitting antenna module surrounded by the plurality of receiving antennae.

8. The sensing system as claimed in claim 1, wherein for the at least one transmitting antenna of the transmitting antenna module and the plurality of receiving antennae at the receiving end respectively have a comb-shaped structure.

9. The sensing system as claimed in claim 1, wherein each sensor of the plurality sensors further includes a delay circuit and a signal analyzing module of the plurality of signal analyzing modules, and the delay circuit generates a reference signal according to the measuring signal.

10. The sensing system as claimed in claim 9, wherein the signal analyzing module included in the sensor further includes:
    a mixer circuit coupled to the delay circuit and one of the plurality of receiving antenna, and mixing the reflected signal and the reference signal to be a mixing signal;
    a signal amplifying circuit coupled to the mixer circuit, and amplifying the mixing signal to be an amplified mixing signal;
    a band pass filtering circuit coupled to the signal amplifying circuit and performing a filtering operation on the amplified mixing signal to generate a filtered signal; and a sampling circuit coupled to the band pass filtering circuit and performing a sampling operation on the filtered signal to obtain an object active state signal.

11. The sensing system as claimed in claim 1, wherein the sensing system is implemented by a chip, and the chip integrates the at least one transmitting antenna, the plurality of receiving antennae, and an integrated circuit having the one or more overshoot and undershoot wave generating circuits and the plurality of sensors.

12. The sensing system as claimed in claim 1, wherein the sensing system further includes a signal processing device, and the signal processing device further includes: a wireless module that communicates with the plurality of sensors; and a microcontroller that applies a calculation unit to calculate one or more pressures of the target object.

13. The sensing system as claimed in claim 12, wherein the calculation unit uses an algorithm to calculate one or more blood pressures, and the algorithm includes a relation formula between the one or more pressures and a pulse wave velocity (PWV), and the PWV is a measure for two measure points of the target object.

14. The sensing system as claimed in claim 13, wherein the PWV is expressed as a function of a distance between two different receiving antennae of the plurality of antennae, and a time difference of two signals received by two different sensors of the plurality of sensors, respectively.

15. The sensing system as claimed in claim 14, wherein the time difference is a time lapse obtained through two different generating times of two different pulse peaks received by the two different antennae.

16. A sensing method for physiology measurements of blood pressure or pulse wave velocity, comprising:
    at a transmission end, generating, with each of a plurality of overshoot and undershoot wave generating circuits, a measuring signal according to a Pulse Width Modulation (PWM) signal, and emitting, with each of at least one transmitting antenna, the measuring signal to a target object, wherein the measuring signal has a characteristics of a pulse wave, and overshoot and undershoot waves are also on the pulse wave;
    at a receiving end, receiving, with each of a plurality of receiving antennae, a reflected signal reflected by the target object;
    generating, by a plurality of signal analyzing modules respectively included in a plurality of sensors, a plurality of object active state signals by analyzing the reflected signal from the each receiving antenna; and
    transmitting the plurality of object active state signals simultaneously or non-simultaneously to a digital signal processing device, wherein the measuring signal is in a form of a radiation capable of being reflected from a physical body having blood flowing therein.

17. The sensing method as claimed in claim 16, wherein the measuring signal is generated by generating the PWM signal according to a clock signal, and modulating the PWM signal to be the measuring signal with the overshoot and undershoot pulses by means of a digital signal processing.

18. The sensing method as claimed in claim 16, wherein an asymmetric comb-shaped antenna module, or various variations regarding the asymmetric comb-shaped antenna module is used as at least one transmitting antenna of a transmitting antenna module and the plurality of receiving antennae at the receiving end.

19. The sensing method as claimed in claim 16, the sensing method further performs a calculation of a pressure measurement of the target object, and the calculation of the pressure measurement includes: calculating a pulse time difference of a first pulse peak and a second pulse peak, wherein the first pulse peak and the second pulse peak are received by two different receiving antennae of the plurality of receiving antennae; calculating a pulse wave velocity (PWV) by using the pulse time difference and a distance between the first pulse peak and the second pulse peak; and calculating each pressure of one or more pressures, by expressing a linear relation between the pressure and the pulse wave velocity.

20. The sensing method as claimed in claim 19, wherein the pressure measurement is chosen from one or more combinations of a blood pressure measurement of a plurality of main arteries of a chest, a blood pressure measurement of a plurality of carotid arteries of a neck, a brain pressure measurement, a blood pressure measurement of a peripheral vascular.

* * * * *